United States Patent [19]

Cartmell et al.

[11] Patent Number: 5,059,424
[45] Date of Patent: Oct. 22, 1991

[54] HYDROGEL WOUND DRESSING PRODUCT

[75] Inventors: James V. Cartmell; Wayne R. Sturtevant, both of Centerville, Ohio; Manuel Valadez, Castaic, Calif.; Michael L. Wolf, West Milton, Ohio

[73] Assignee: NDM Acquisition Corp., Minneapolis, Minn.

[21] Appl. No.: 430,188

[22] Filed: Nov. 1, 1989

[51] Int. Cl.⁵ .............................................. A61F 13/00
[52] U.S. Cl. .................................. 424/443; 128/156; 524/310
[58] Field of Search .......................... 424/28, 132, 443; 260/29.2; 128/156, 132 D; 524/310

[56] References Cited

U.S. PATENT DOCUMENTS

| | | | |
|---|---|---|---|
| 3,526,224 | 6/1967 | Potts | 128/155 |
| 3,543,750 | 1/1968 | Meizaris | 128/155 |
| 3,579,628 | 5/1971 | Gander et al. | 424/445 |
| 4,061,618 | 12/1977 | Stanley et al. | 260/29.2 |
| 4,226,232 | 10/1980 | Spence | 128/155 |
| 4,393,048 | 7/1983 | Mason, Jr. et al. | 424/132 |
| 4,460,369 | 7/1984 | Seymour | 128/132 |
| 4,517,326 | 5/1985 | Cordts et al. | 523/113 |
| 4,538,603 | 9/1985 | Pawelchak et al. | 128/156 |
| 4,595,001 | 6/1986 | Potter et al. | 128/156 |
| 4,657,006 | 4/1987 | Rawlings et al. | 128/156 |
| 4,669,458 | 6/1987 | Abraham et al. | 128/133 |
| 4,704,119 | 11/1987 | Shaw et al. | 604/304 |
| 4,743,249 | 5/1988 | Loveland | 604/896 |
| 4,747,401 | 5/1988 | Potter et al. | 128/155 |
| 4,753,232 | 1/1988 | Ward | 128/156 |
| 4,909,244 | 3/1990 | Quarfoot et al. | 128/156 |

FOREIGN PATENT DOCUMENTS

| | | |
|---|---|---|
| 144803 | 3/1986 | European Pat. Off. |
| 2347299 | 4/1975 | Fed. Rep. of Germany |
| 88018877 | 3/1988 | PCT Int'l Appl. |
| 2198441 | 6/1988 | United Kingdom |

OTHER PUBLICATIONS

Smith & Nephew advertisment describing Flexigrid Application System, copyright 1990.
Smith & Nephew Abstract of lecture presented at Advanced Wound Care Symposium, Mar. 12, 1990.

Primary Examiner—Thurman K. Page
Assistant Examiner—William E. Benston, Sr.
Attorney, Agent, or Firm—Killworth, Gottman, Hagan & Schaeff

[57] ABSTRACT

A wound dressing product is described which includes a flexible backing member that can be vacuum formed to include a depression. A pressure-sensitive adhesive layer extends across the depression side of the flexible backing member. A hydrogel material is positioned in the depression of the flexible backing member and a release liner extends over the exposed pressure-sensitive adhesive layer and the exposed hydrogel material, which release liner has a selective releasability whereby it can be removed from the wound dressing product intact, leaving a portion of the pressure-sensitive adhesive and the hydrogel material exposed.

6 Claims, 2 Drawing Sheets

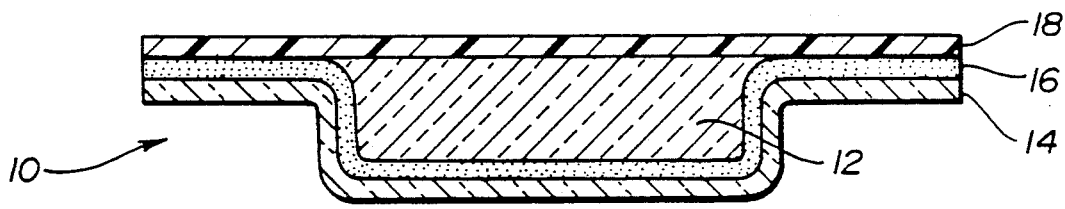
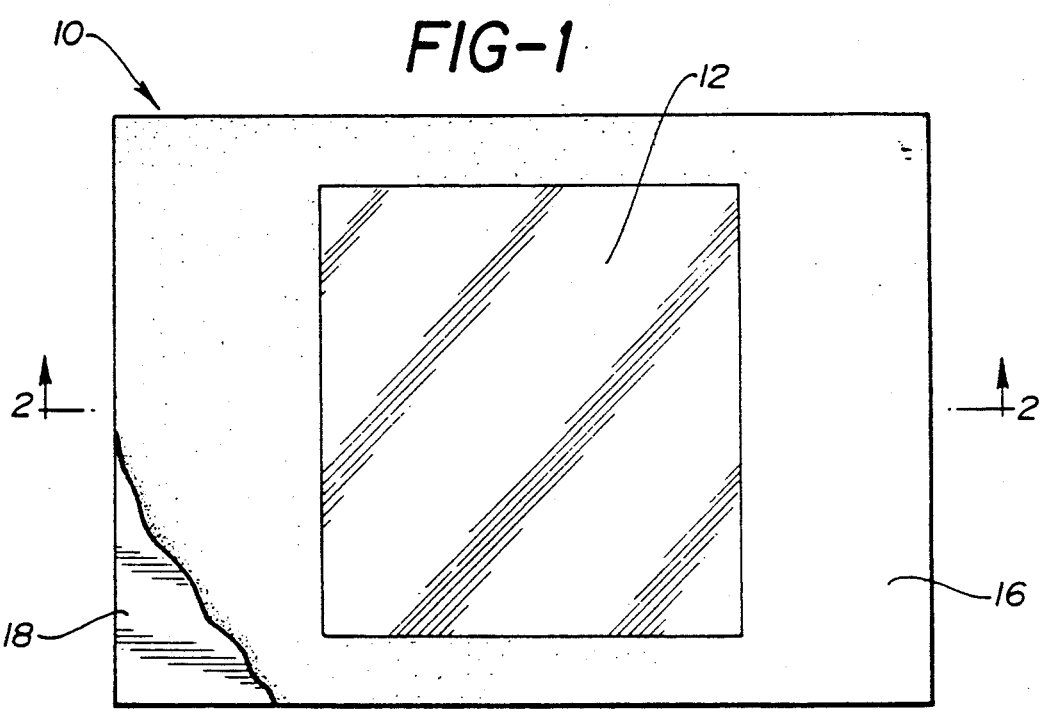
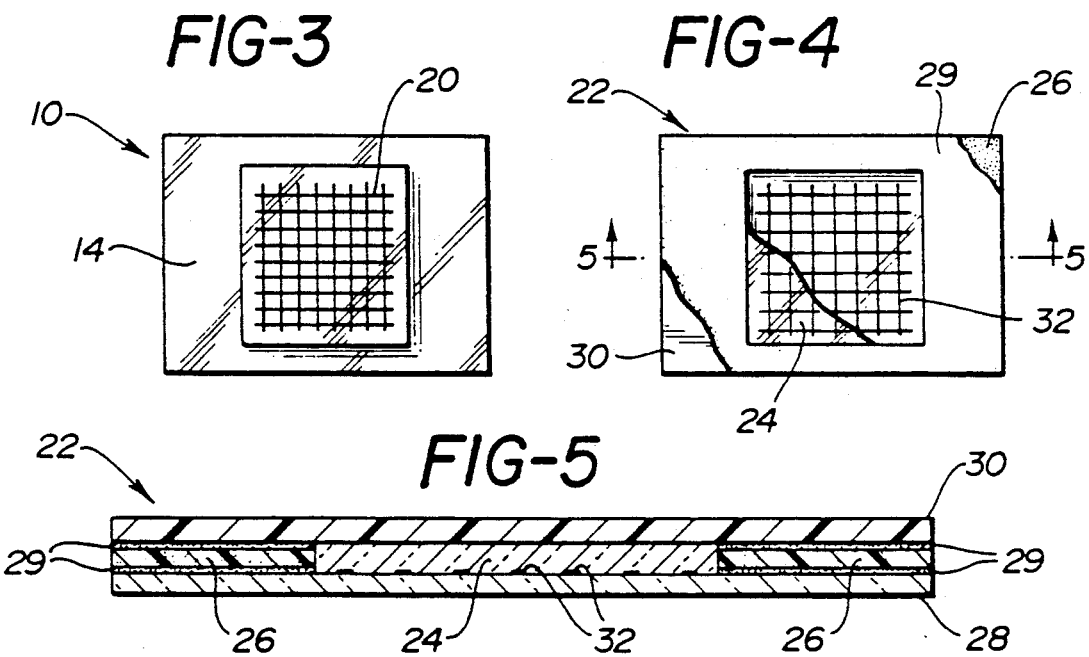

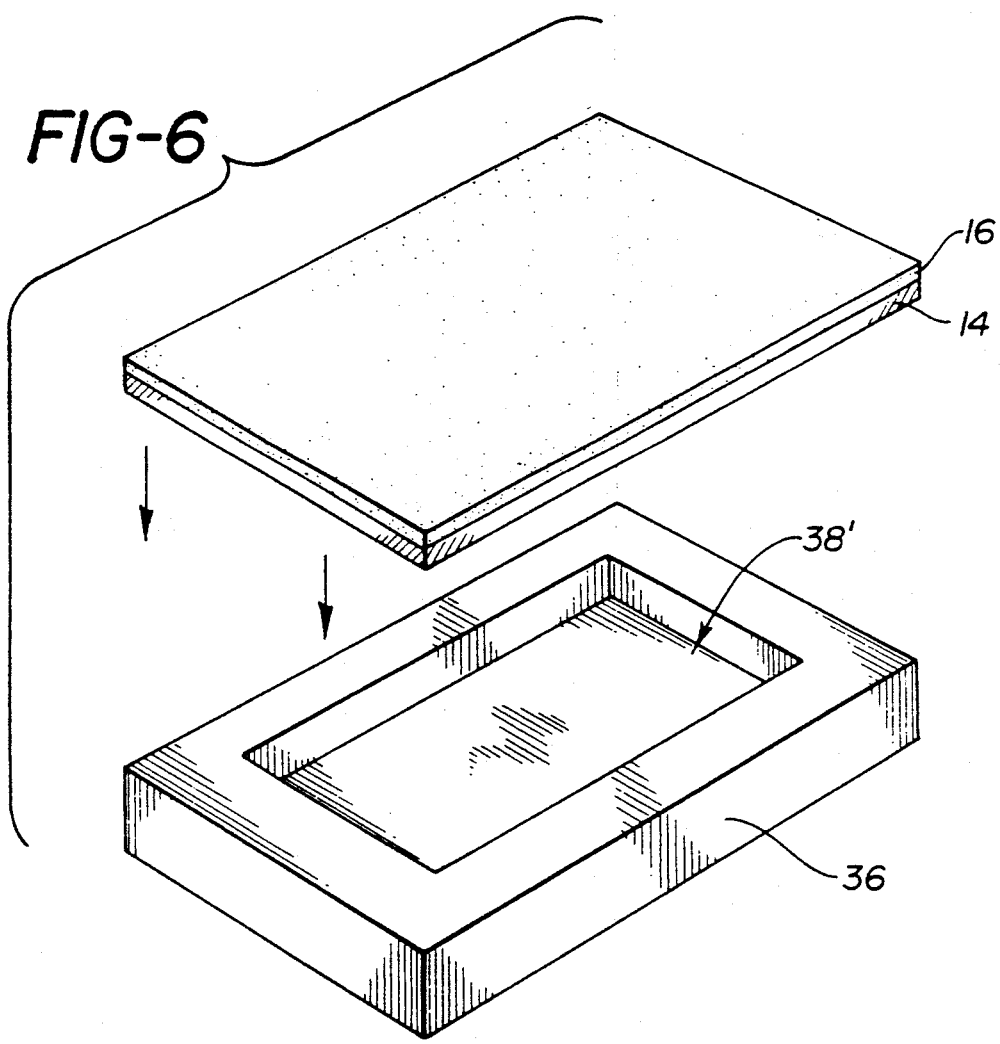
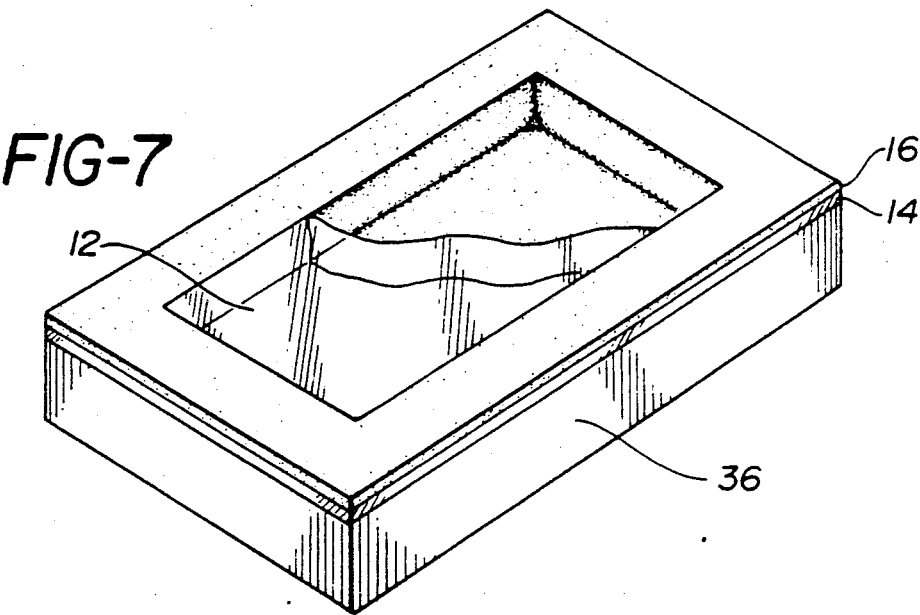

HYDROGEL WOUND DRESSING PRODUCT

BACKGROUND OF THE INVENTION

This invention relates to wound dressings and, more particularly, to a flexible wound dressing product containing a hydrogel substance. The wound dressing product contours to a wound site while maintaining the wound in a moist state.

Managing draining wounds such as decubitus ulcers has presented a difficult problem of treatment for the medical profession. The accumulation of wound exudate, such as blood, serum and purulent matter in the crevices of a wound can lead to bacterial growth which can delay healing of the wound. However, it has been difficult to maintain the wounds free of wound secretion to permit them to heal. Conversely, it is often desirable to allow a wound to heal in a slightly moist state as it is believed that this may accelerate healing.

Currently, there are wound exudate absorption compositions which are comprised of hydrogel materials in powder form. Generally, such dry, powdery hydrogel materials are introduced to an open, draining wound to absorb the exudate from the wound. One such commercially available method of treatment employing dry hydrogel material is the use of Dextranomer beads. Dextranomer beads are highly hydrophilic and comprise spherical beads which can be introduced to a wound site to absorb the wound exudate. A drawback of such hydrogel material is that the dry material can tend to clump and form lumps prior to and during introduction of the material to the wound site. The clumping or lumping can also occur after introduction of the material to the wound site and as it absorbs the wound exudate. The lumps or granules are difficult to apply evenly to the wound and, subsequently, are difficult to remove from the wound site without damaging the new tissue that forms at the wound site.

U.S. Pat. No. 4,226,232, issued to Spence on Oct. 7, 1980, teaches the blending of a hydrogel material with a liquid curing agent, such as a polyethylene glycol prior to introducing the gel-like or salve-like material to a wound. Again, there are drawbacks with such a system, as the system cannot be sterilized by irradiation due to the formation of free radicals within the gel material.

A need has arisen for a wound dressing which can provide a protective covering to the wound while being able to absorb the exudate from the wound. It would be desirable to have a wound dressing which could provide a protective pad over the wound to prevent debris and foreign matter from contaminating the wound and which could cushion the wound against pressure. It would be desirable to have a wound dressing which would not adhere to the new tissue forming in the wound or the exudate being released by the wound. It would be desirable to have a wound dressing which would be transparent to enable observation of the healing process of the wound, but which would shield the wound against bacteria to inhibit infection. It would also be desirable to have a wound dressing wherein through selecting a carrier film could either permit moisture so that the wound environment is stabilized with respect to moisture presence or occlude moisture transfer.

It would also be desirable to provide a wound dressing which could be precut, sterilized, and readily available for application to a draining wound. Such a wound dressing could be readily applied by an attendant without the need for mixing and applying a paste or gel to an open wound. Such a wound dressing system could save time and expense and insure a uniform, consistent coating. It would further be desirable to have such a wound dressing which could be radiation sterilized as current gas sterilization techniques are coming under more and more restrictions and closer scrutiny for environmental reasons.

SUMMARY OF THE INVENTION

The invention herein is directed to a wound dressing which can be manufactured to any desirable size to provide a dressing for any size open, draining wound. The invention herein is directed to a wound dressing which will absorb the exudate from the wound but which will not adhere to the wound. Thus, when it is removed from the wound it will not damage the wound. The wound dressing provides a clear, wet wound dressing which allows visual inspection of the wound without having to remove the dressing.

In particular, the present invention includes a method of treating wounds comprising the step of applying a substantially transparent hydrogel material to a wound site, the hydrogel material comprising from about 15% to about 30% by weight of a polyhydric alcohol selected from the group consisting of polypropylene glycol, polyethylene glycol and glycerine, from about 8% to about 14% by weight of an isophorone diisocyanate terminated prepolymer, from about 5% to about 10% by weight of a polyethylene oxide based diamine, up to about 1% by weight of a salt such as sodium chloride, and the balance water.

In a preferred embodiment of the present invention, the hydrogel composition comprises 17% by weight of the polyhydric alcohol, 12% by weight of the isophorone diisocyanate terminated prepolymer, 9% by weight of the polyethylene oxide based diamine, 1% by weight of the salt, and the balance water.

The present invention also discloses a wound dressing product for application to a wound site. The wound dressing product comprises: a flexible backing member having a first side and a second side and further having a vacuum formed center portion to define a depression on the first side; a pressure-sensitive adhesive layer extending across the first side of the flexible backing member; a hydrogel material located in the depression of the flexible backing member; and a release liner extending over the exposed pressure-sensitive adhesive layer and the exposed hydrogel material.

A release liner extends over the exposed pressure sensitive adhesive layer and the exposed hydrogel. The release liner has a selective releasability such that it can be removed from the wound dressing to expose the pressure sensitive adhesive and the hydrogel. The pressure sensitive adhesive is exposed along an area which forms a perimeter surrounding the hydrogel.

In a preferred embodiment of the present invention, the flexible backing member comprises a polyurethane film and the pressure-sensitive adhesive comprises an acrylic-based adhesive. Additionally, the wound dressing product further comprises a printed wound sizer on the flexible backing member overlying the hydrogel material.

Another embodiment of the present invention discloses a similar wound dressing product. This similar wound dressing product comprises: a flexible backing sheet; a perimeter-defining, damming layer on the flexible backing member having a central cavity; and a hydrogel material comprising from about 15% to about 30% by weight of a polyhedric alcohol, from about 8% to about 14% by weight of an isophorone diisocyanate terminated prepolymer, from about 5% to about 10% by weight of a polyethylene oxide based diamine, up to about 1% by weight of a salt, and the balance water.

In a preferred embodiment of this wound dressing product, the hydrogel comprises 17% by weight of the polyhydric alcohol, 12% by weight of the isophorone diisocyanate terminated prepolymer, 9% by weight of the polyethylene oxide based diamine, 1% by weight of the salt, and the balance water.

The invention herein also includes a method of manufacturing a wound dressing which is moist, transparent, and radiation sterilizable. The method includes coating a flexible carrier film with a pressure sensitive adhesive. The flexible carrier film can be occlusive or permeable to moisture vapor flow. The pressure sensitive adhesive coated flexible carrier film is laid in a cavity of a vacuum platen with the adhesive coated surface facing upward and the non-adhesive faced surface of the film is laid across the vacuum platen. A vacuum is pulled through the vacuum platen. The vacuum draws the flexible carrier film into the depression on the vacuum platen creating a corresponding cavity in the film. A hydrogel material is then introduced to the cavity to fill it with the hydrogel. The hydrogel sets. The hydrogel can be in a fluid state when it is introduced to the cavity. The hydrogel cures or sets to a gel-like consistency. The vacuum is withdrawn after the hydrogel has set to the gel-like consistency. The depression remains containing the gel-like hydrogel material. A release liner can be applied to cover the exposed adhesive surface of the flexible backing member and the exposed hydrogel in the cavity. The release liner can have a selective releasability such that it can be removed from the adhesive and hydrogel without tearing or violating the integrity of the hydrogel or adversely impacting the adhesive properties of the pressure sensitive adhesive.

The method of manufacturing the wound dressing product of the present invention comprises the steps of: providing a flexible film, the flexible film having a first side and a second side; coating the first side of the flexible film with a pressure-sensitive adhesive capable of adhering to the skin of a patient; introducing the second side of the flexible film to a vacuum platen, the vacuum platen defining a center cavity portion in the first side of the flexible film; pulling a vacuum on the vacuum platen to draw the first side of the adhesive coated flexible film into the center cavity portion; dispensing a hydrogel material into the center cavity portion formed on the first side of the adhesive coated flexible film; and attaching a release liner over the first side of the adhesive coated flexible film. Additionally, the method of manufacturing the wound dressing product may further include the step of printing a pattern on the flexible backing member overlying the hydrogel material, thereby creating a wound sizer permitting measurement of the size of a wound.

BRIEF DESCRIPTION OF THE DRAWINGS

FIG. 1 is a plan view of the wound dressing product viewing the surface which is to be applied on the patient;

FIG. 2 is a cross-sectional view of the wound dressing product of FIG. 1 taken along lines 2—2;

FIG. 3 is a plan view of another embodiment of a wound dressing product as viewed from the exposed side of the wound dressing product when the wound dressing product is applied to a patient;

FIG. 4 is a plan view of another embodiment of the wound dressing product herein, showing the non-patient side of the dressing;

FIG. 5 is a cross-sectional view of the wound dressing product embodiment shown in FIG. 4 taken along lines 5—5;

FIG. 6 is a perspective view of a vacuum platen which can be used to form the wound dressing product such as shown in FIG. 1; and FIG. 7 is a perspective view illustrating the method of forming a wound dressing product such as shown in FIG. 1.

DETAILED DESCRIPTION OF THE INVENTION

The wound dressing product herein will be described with regard to the accompanying drawings. In particular, with reference to FIGS. 1 through 3, preferred embodiments of the wound dressing product 10 are illustrated. The wound dressing product includes a hydrogel material 12 which will be in contact with the wound when the wound dressing product is placed on a patient. The hydrogel material 12 is maintained in a cavity 38 which is formed in a flexible membrane 14. The flexible membrane 14 serves as the carrier or substrate for the hydrogel 12. The flexible membrane 14 also serves as a protective layer for the wound dressing product 10 when the wound dressing product 10 is applied to a wound on a patient. The flexible membrane 14 may be any material which is moisture vapor permeable so that when the wound dressing product 10 is placed on a wound, it will permit the hydrogel 12 and thereby the wound covered by the hydrogel 12 to release moisture. The use of a moisture vapor permeable material prevents undue moisture build-up at the wound site. In some instances it is desirable to use an occlusive film to retain moisture in the healing wound.

The flexible membrane 14 also serves as a substrate which can aid in the adhering of the wound dressing product 10 to the patient. The flexible membrane 14 is coated with an adhesive layer 16. The adhesive layer 16 may be any suitable adhesive and preferably a pressure-sensitive adhesive that is capable of being in contact with the human body without causing any harmful effects. Acceptable pressure-sensitive adhesives include acrylate based adhesives.

The hydrogel 12 is positioned within the cavity 38 of the flexible membrane 14. The cavity 38 is formed within the perimeter of the side edges of the flexible membrane 14, creating a perimeter of exposed flexible membrane around the hydrogel 12. The exposed flexible membrane provides an exposed surface area surrounding the hydrogel 12, which exposed surface area is coated with the adhesive 16. The adhesive layer 16 forming a perimeter around the hydrogel 12 aids in the securing of the wound dressing product 10 to a patient. The exposed hydrogel 12 also serves as an anchoring adhesive for the wound dressing product on the patient. Thus, the hydrogel 12 and pressure-sensitive adhesive 16 provide two distinct anchoring adhesives for the wound dressing product 10.

Referring to FIG. 2, a protective release liner 18 is laminated on the wound dressing product 10 to protect the sterility of the pressure-sensitive adhesive 16 and the hydrogel 12 of the wound dressing product 10 prior to the wound dressing product 10 being applied. The protective release liner 18 is a removable protective release liner which has a selective releasability such that it may be readily removed from its contact with the pressure-sensitive adhesive 16 and the hydrogel 12 without destroying the adhesive properties of the pressure-sensitive adhesive 16 or destroying the integrity of the hydrogel 12.

The flexible membrane 14 may be constructed from any suitable material which can provide a backing to a wound dressing. The flexible membrane 14 may be a polymeric elastic or flexible film coating providing a bacterial barrier and formed from a water vapor permeable pliable elastomer material such as a flexible polyurethane, polyacrylate, polyethylene and the like. A polyurethane film is the preferred material for the flexible membrane 14. For an occlusive film, a polypropylene or co-polyester can be used.

The hydrogel 12 is a hydrogel material which comprises from about 15% to about 30% by weight of a polyhedric alcohol selected from the group consisting of polypropylene glycol, polyethylene glycol and glycerine. The hydrogel 12 further includes from about 8% to about 14% of an isophorone diisocyanate terminated prepolymer with about 3% NCO content. The hydrogel 12 also includes from about 5% to about 10% by weight of a diamine, with the preferred diamine being a polyethylene oxide based diamine. The hydrogel 12 further includes up to about 1% by weight of a salt such as sodium chloride. The balance of the hydrogel material 12 is comprised of water.

In a preferred embodiment of the present invention, the hydrogel material 12 comprises 17% by weight of the polyhydric alcohol, 12% by weight of the isophorone diisocyanate terminated prepolymer, 9% by weight of the polyethylene oxide based diamine, 1% by weight of the salt, and the balance water.

The manufacture of similar hydrogel material is disclosed in U.S. Pat. No. 4,517,326, the disclosure of which is incorporated herein by reference. A similar method may be used to create the hydrogel herein except for the material contents.

Since the hydrogel material 12 herein is transparent, a wound sizer can be incorporated in the wound dressing product 10. With regard to FIG. 3, there is shown another embodiment of a wound dressing product 10 herein. The wound dressing product 10 shown in FIG. 3 uses similar reference numerals to refer to the similar components as discussed with regard to the wound dressing product 10 embodiment shown in FIGS. 1 and 2. FIG. 3 shows a plan view of a wound dressing product 10 looking at the non-patient, contact surface of the wound dressing product 10. The wound dressing product 10 has a flexible membrane 14 and a hydrogel area. Printed on the flexible membrane 14 is a grid which functions as a wound sizer 20. The wound sizer 20 may have any grid-like pattern which can be used for measuring the size of a wound. Shown in FIG. 3 is a rectangular grid pattern, but a circular grid pattern could also be used. The transparent hydrogel material 12 permits observation of the wound, and the wound sizer 20 printed on the flexible membrane 14 permits observation of changes in the wound size while the wound dressing product 10 is in use. Although the wound sizer 20 in FIG. 3 is shown as being printed only in the hydrogel area, it may be printed over the entire wound dressing product 10 or any portion thereof.

A step in the manufacturing process of the wound dressing product 10 shown in FIGS. 1 through 3 is illustrated in FIGS. 6 and 7. With regard to FIG. 6, there is shown in exploded view of a processing step in the manufacturing process for the wound dressing product 10. The wound dressing product 10 is manufactured using a vacuum platen 36 which has a cavity 38 formed thereon. The cavity 38 is cut into the platen 36 in any size that is desirable for the hydrogel material 12 of the wound dressing product 10. The size of the cavity 38 may be selected based upon the end use of the wound dressing product 10. For the hydrogel material 12 herein, the size can vary as the hydrogel material 12 readily cures and maintains its integrity, regardless of the area of the hydrogel 12, when formed to a depth sufficient for the wound dressing product 10 herein.

The flexible membrane 14, with the adhesive side facing upwardly, is placed in contact with the vacuum platen 36. A vacuum pump (not shown) in communication with the platen 36, creates a partial vacuum in the platen 36 which is sufficiently strong to form the flexible membrane 14 to the contour of the cavity 38 in the vacuum platen 36. The partial vacuum is also sufficient to hold the flexible membrane 14 in place against the vacuum platen 36, as the flexible membrane 14 assumes the size and shape of the cavity 38.

Upon forming the cavity 38, the hydrogel material 12 is dispensed into the cavity 38 overlying and covering the adhesive coating 16 on the flexible membrane 14. The hydrogel 12 is dispensed to uniformly fill the cavity 38. The vacuum is maintained until the hydrogel 12 sufficiently sets so that movement of the flexible membrane 14 does not violate the integrity of the hydrogel 12, nor does the hydrogel 12 tend to flow or run out of the cavity 38. Generally, the vacuum need not be maintained as the weight of the hydrogel 12 is sufficient force to retain the shape of the cavity 38 when using the thin films employed herein. Generally, the hydrogel 12 is formed in about a ⅛ inch thickness which is suitable for most wounds, but other thicknesses may be used depending upon the final use of the wound dressing product 10.

FIG. 7 shows the adhesive-coated flexible membrane 14 formed in the vacuum platen 36 with the hydrogel 12 filling the cavity 38 and leaving an adhesive coated edge of the flexible membrane 14 exposed around the hydrogel 12. The hydrogel 12 herein readily sets such that upon release of the vacuum the hydrogel 12 will retain its integrity such that movement of the film/hydrogel interface will not disturb the integrity of the hydrogel layer 12 which remains substantially intact. A protective cover or release liner 18 may be placed over the assembly and the entire construction can be die cut to the desired overall size for the wound dressing product 10.

Another embodiment of the wound dressing product herein is shown in FIGS. 4 and 5. FIG. 4 shows a wound dressing product 22 which includes a hydrogel layer 24 forming a wound covering and wound exudate absorbing layer. The hydrogel layer 24 may be a hydrogel material such as discussed with regard to FIGS. 1 through 3.

The hydrogel layer 24 is formed over a carrier substrate layer or flexible backing sheet 28 which may be constructed of any moisture vapor permeable material such as a polyurethane. The flexible backing sheet 28 is similar to the flexible membrane 14 in the embodiment shown in FIGS. 1 through 3 and may be any of the materials described with regard to that embodiment. The structure for the wound dressing product shown in FIG. 4 is shown in the cross-sectional view of FIG. 5.

With regard to FIGS. 4 and 5, the hydrogel layer 24 is maintained in place on the flexible backing sheet 28 by a perimeter-defining damming layer, such as a foam dam 26 which overlies the substrate layer 28. The foam dam 26 has a sufficient height to support the hydrogel layer 24 when the hydrogel material is deposited on the flexible backing member 28. The foam dam 26 may be constructed of any suitable material which will be biocompatible with the body. A preferred material is polyethylene foam. The foam dam 26 may be coated on both of its surfaces, with a suitable adhesive 29. The adhesive coated on the patient side may be different than the adhesive on the flexible backing sheet side. That is, the adhesive properties for adhering the foam dam 26 to the flexible backing sheet may be different than those for adhering the foam dam 26 to a patient's skin. A release liner 30 may be coated over the exposed hydrogel and foam dam 26 member.

For adhering the wound dressing product 22 to a patient, the foam dam member 26 may be coated with a pressure-sensitive adhesive on its surface facing the release liner 30. The pressure-sensitive adhesive may be a pressure-sensitive adhesive such as described with regard to the embodiment in FIGS. 1 and 2. The hydrogel material also may act as an adhesive to aid in adhering the wound dressing product 22 to a patient.

The release liner 30 may be any suitable material having release properties for selectively being releasable from the hydrogel and foam dam without destroying the integrity of the hydrogel or foam dam. As shown in FIG. 4, the flexible backing may be imprinted with a printed wound sizer 32. As with the earlier embodiment, the hydrogel material 24 in the embodiment shown in FIGS. 4 and 5 is a clear hydrogel material which will permit viewing of the wound underneath the hydrogel material 24 when the wound dressing product 22 is in place. The grid or printed wound sizer 32 permits observation of the wound and monitoring of the changes in size of the wound.

The hydrogel wound dressing product herein provides a benefit not currently realizable in state-of-the-art wound dressings. The hydrogel material is capable of absorbing wound exudate. The hydrogel material is clear and can permit visual observation of the wound. The hydrogel material retains its integrity such that upon removal of the wound dressing, no gel or wound debris is left in the wound. The hydrogel material has physical properties which permit it to be non-traumatically removed from a wound. The hydrogel material also cushions the wound against pressure which can be exerted on the outer surface of the wound dressing when the wound dressing is worn by the patient. The hydrogel material herein is also advantageous in that it permits extended wearing of the dressing by a patient due to the water absorption that is provided by hydrogel material. The hydrogel material of the present invention has a salt content approximating that of the human body, and this may enhance its ability for extended wearing.

The hydrogel herein is particularly suited for use as part of a wound dressing product. The hydrogel is a moist hydrogel, containing more than 50% by weight of water, and is capable of providing some adhesiveness to the wound dressing product. However, the adhesive property of the hydrogel is not such that it will damage cell or tissue growth deleteriously, upon removal of the wound dressing product from the wound. That is, the hydrogel provides an adhesive tenacity to aid in adhering the wound dressing product to the patient and wound site. The hydrogel exhibits a high degree of fluid absorption and can thereby absorb a sufficiently large quantity of wound exudate.

Another advantage of the hydrogel material herein is that it retains its gel-like integrity even upon removal of the wound dressing product from a wound site. The hydrogel does not leave debris, such as hydrogel particles, in the wound upon removal. The hydrogel material herein also exhibits a capability of non-traumatically releasing from the wound when the wound dressing product is removed from the wound. This non-traumatic release of the hydrogel wound dressing product from the wound does not destroy the new cell tissue forming at the wound site and thereby wound healing is not inhibited when the dressing is removed. The hydrogel material can also provide a protective cushioning of the wound due to its gel-like consistency.

A further advantage of the hydrogel herein is its ability to absorb water. It can remain on a wound for relatively long periods of time and, therefore, does not need to be removed frequently. Finally, a special advantage of the hydrogel material herein is that the hydrogel material is clear. That is, the hydrogel material is not only translucent but also transparent. The hydrogel material is sufficiently clear such that visual inspection of the wound can be performed without having to remove the wound dressing product. Although the hydrogel material does not deleteriously affect the wound when it is removed, it is still highly desirable to avoid removing dressings from a wound site, as removal can provide an opportunity for the ingress of bacteria to the wound from the surrounding environment.

Having described the invention in detail and by reference to preferred embodiments thereof, it will be apparent that modifications and variations are possible without departing from the scope of the invention which is defined in the appended claims.

What is claimed is:

1. A wound dressing product comprising:
   a flexible backing member having a first side and a second side and further having a vacuum formed center portion to define a depression on said first side;
   a pressure-sensitive adhesive layer extending across said first side of said flexible backing member;
   a hydrogel material located in said depression of said flexible backing member, said hydrogel material comprises from about 15% to about 30% by weight of a polyhydric alcohol, from about 8% to about 14% by weight of an isophorone diisocyanate terminated prepolymer, from about 5% to about 10% by weight of a polyethylene oxide-based diamine, from about 0% to about 1% by weight of a salt, and the balance water; and
   a release liner extending over said exposed pressure-sensitive adhesive layer and said exposed hydrogel material.

2. A wound dressing product comprising:
   a flexible backing sheet;
   a perimeter-defining, damming layer on the flexible backing member having a central cavity; and
   a hydrogel material comprising from about 15% to about 30% by weight of a polyhydric alcohol, from about 8% to about 14% by weight of an isophorone diisocyanate terminated prepolymer, from about 5% to about 10% by weight of a polyethylene oxide based diamine, up to about 1% by weight of a salt, and the balance water.

3. A wound dressing product as claimed in claim 2 wherein said hydrogel comprises:

17% by weight of said polyhydric alcohol;

12% by weight of said isophorone diisocyanate terminated prepolymer;

9% by weight of said polyethylene oxide based diamine;

1% by weight of said salt; and the balance water.

4. A wound dressing product as claimed in claim 2 wherein said flexible backing sheet comprises a polyurethane film.

5. A wound dressing product as claimed in claim 2 wherein said hydrogel material is transparent.

6. A wound dressing product as claimed in claim 2 further comprising a printed wound sizer on said flexible backing sheet overlying said hydrogel material.

* * * * *